United States Patent
Murphy et al.

(10) Patent No.: US 10,725,026 B2
(45) Date of Patent: *Jul. 28, 2020

(54) METHOD FOR PREDICTING RISK OF EXPOSURE TO INTERSTITIAL FIBROSIS AND TUBULAR ATROPHY WITH CLUSTERIN

(71) Applicants: Icahn School of Medicine at Mount Sinai, New York, NY (US); Westmead Institute For Medical Research, Westmead, NSW (AU); Western Sydney Local Health District, Westmead, NSW (AU)

(72) Inventors: Barbara Murphy, Boston, MA (US); Philip J. O'Connell, Sydney (AU)

(73) Assignees: Icahn School of Medicine at Mount Sinai, New York, NY (US); Westmead Institute For Medical Research, Westmead (AU); Western Sydney Local Health District, Westmead (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/810,861

(22) Filed: Nov. 13, 2017

(65) Prior Publication Data
US 2018/0292395 A1    Oct. 11, 2018

Related U.S. Application Data

(63) Continuation of application No. 14/394,965, filed as application No. PCT/US2013/037002 on Apr. 17, 2013, now Pat. No. 9,816,985.

(60) Provisional application No. 61/625,636, filed on Apr. 17, 2012.

(51) Int. Cl.
| | | |
|---|---|---|
| G01N 33/50 | (2006.01) | |
| G01N 33/53 | (2006.01) | |
| A61P 13/12 | (2006.01) | |
| G01N 33/68 | (2006.01) | |
| C07K 14/47 | (2006.01) | |

(52) U.S. Cl.
CPC .......... *G01N 33/5308* (2013.01); *A61P 13/12* (2018.01); *G01N 33/50* (2013.01); *G01N 33/6893* (2013.01); *C07K 14/47* (2013.01); *C07K 14/4705* (2013.01); *G01N 2333/775* (2013.01); *G01N 2800/085* (2013.01); *G01N 2800/245* (2013.01); *G01N 2800/50* (2013.01); *G01N 2800/54* (2013.01)

(58) Field of Classification Search
None
See application file for complete search history.

(56) References Cited

U.S. PATENT DOCUMENTS

| | | |
|---|---|---|
| 2005/0272649 A1 | 12/2005 | Hruska et al. |
| 2011/0020367 A1 | 1/2011 | Strom et al. |
| 2011/0065608 A1 | 3/2011 | Labrie et al. |
| 2011/0177959 A1 | 7/2011 | Spain et al. |

OTHER PUBLICATIONS

Cappelletti et al., "Patterns and changes in gene expression following neo-adjuvant anti-estrogen treatment in estrogen receptor-positive breast cancer," Endocrine-Related Cancer, 2008, 15: 439-449.
Cochrane et al., "Differential regulation of clusterin and its isoforms by androgens in prostate cells," Journal of Biological Chemistry, 2007, 282: 2278-2287.
De Beuf et al., "Epoetin delta as an antifibrotic agent in the remnant kidney rat: a possible role for transforming growth factor beta and hepatocyte growth factor," Nephron Exp Nephroi., 2010, 115: e46-e59.
De Silva et al., "Apolipoprotein J: structure and tissue distribution," Biochemistry, 1990, 29: 5380-5389.
Devauchelle et al., "Characterization and functional consequences of underexpression of clusterin in rheumatoid arthritis," J Immunol., 2006, 177: 6471-6479.
Isoniemi et al., "Histological chronic allograft damage index accurately predicts chronic renal allograft rejection," Transplantation, Dec. 1994, 1195-1198.
Jenne and Tschopp, "Molecular structure and functional characterization of a human complement cytolysis inhibitor found in blood and seminal plasma: identity to sulfated glycoprotein 2, a constituent of rat testis fluid," PNAS, 1989, 86: 7123-7127.
'Hitocompatibilityandimmunogenetics.com' [online]. "Histocompatibility & Immunogenetics—a collection of brief revision notes," Aug. 8, 2012, [retrieved on Apr. 17, 2017]. Retrieved from the Internet: URL <http://www.histocompatibilityandimmunogenetics.com/>. 2 pages.
Mallory et al., "A novel group of genes regulates susceptibility to antineoplastic drugs in highly tumorigenic breast cancer cells," Molecular Pharmacology, 2005, 68: 1747-1756.

(Continued)

*Primary Examiner* — Zachary C Howard
(74) *Attorney, Agent, or Firm* — Fish & Richardson P.C.

(57) ABSTRACT

A method for identifying a kidney transplant recipient at an increased risk of developing interstitial fibrosis or tubular atrophy which comprises obtaining a post-transplant urine sample from the kidney transplant recipient; measuring the level of clusterin in the urine sample; comparing the level of clusterin in the patient sample to the level of clusterin in a control sample from the urine of a non-fibrotic kidney transplant recipient; diagnosing a kidney transplant recipient with a clusterin level that is significantly higher than the clusterin level in the control as being at an increased risk of developing interstitial fibrosis or tubular atrophy.

16 Claims, 2 Drawing Sheets

(56) References Cited

OTHER PUBLICATIONS

Miyake et al., "Testosterone-repressed prostate message-2 is an antiapoptotic gene involved in progression to androgen independence in prostate cancer," Cancer Research, 2000, 60: 170-176.
Negri, "Prevention of progressive fibrosis in chronic renal diseases: antifibrotic agents," J Nephrol, 2004, 17: 496-503.
Nuutinen et al., "Clusterin: a forgotten player in Alzheimer's disease," Brain Res Rev, Oct. 2009, 61: 89-104.
Reddy et al., "Transforming Growth Factor β (TGFβ)-Induced Nuclear Localization of Apolipoprotein J/Clusterin in Epithelial Cells," Biochemistry, May 1996, 35: 6157-6163.
Redondo et al., "Overexpression of clusterin in human breast carcinoma," American Journal of Pathology, 2000, 157: 393-399.
Rizzi and Bettuzzi, "The Clusterin Paradigm in Prostate and Breast Carcinogenesis," Endocrine-Related Cancer, 2010, 17: R1-R17.
Saverio et al., "Tumor progression is accompanied by significant changes in the levels of expression of polyamine metabolism regulatory genes and clusterin (sulfated glycoprotein 2) in human prostate cancer specimens," Cancer Research, Jan. 2000, 60: 28-34.
Sharman et al., "Challenge and promise: roles for clusterin in pathogenesis, progression and therapy of cancer," Cell Death and Differentiation, 2006, 13: 12-19.
Solez et al., "Banff '05 Meeting Report: Differential Diagnosis of Chronic Allograft Injury and Elimination of Chronic Allograft Nephropathy ('CAN')," American Journal of Transplantation, Mar. 2007, 7: 518-526.
Solez et al., "Banff '07 Classification of Renal Allograft Pathology:Updates and Future Directions," American Journal of Transplantation, Apr. 2008, 753-760.
Wong et al., "Molecular characterization of human TRPM-2/clusterin, a gene associated with sperm maturation, apoptosis and neurodegeneration," European Journal of Biochemistry, 1994, 221: 917-1925.
Zhang et al., "Clusterin inhibits apoptosis by interacting with activated Bax," Nature Cell Biology, Sep. 2005, 909-915.

METHOD FOR PREDICTING RISK OF EXPOSURE TO INTERSTITIAL FIBROSIS AND TUBULAR ATROPHY WITH CLUSTERIN

This application claims priority to U.S. patent application Ser. No. 14/394,965, filed Oct. 16, 2014 which is the U.S. National Phase Application under U.S.C. § 371 of International Patent Application No. PCT/US2013/037002, filed Apr. 17, 2013 which claims the priority of U.S. Provisional Patent Application Ser. No. 61/625,636, filed on Apr. 17, 2012. The contents of the above applications are incorporated herein in their entirety.

GOVERNMENT CLAUSE

This invention was made with government support under AI070107 awarded by The National Institutes of Health. The government has certain rights in the invention.

BACKGROUND OF THE INVENTION

Clusterin (CLU) is a secreted multi-function glycoprotein that has been associated with clearance of debris, apoptosis inhibition, tissue remodeling, complement inhibition, regulation of complement-mediated cell lysis, membrane recycling, cell-cell adhesion and epithelial growth. CLU is a single 9-exon gene expressing three protein forms[1,2,3]. Each of the forms has distinct sub-cellular localizations and biological functions[4,5]; CLU has nearly ubiquitous tissue distribution. Due to functions such as regulatory activity on complement, CLU is involved in inflammation and autoimmunity.

CLU is implicated in a number of disease states including cancer, Alzheimer's disease, and rheumatoid arthritis[6,7,8]. It is overexpressed in several human cancers, and its suppression deems cancer cells sensitive to chemotherapeutic drug-mediated apoptosis[9]. However, despite the many reports on CLU functionality and its relation to tumorigenesis, many contradictions in the data still exist. Understanding the role of CLU in tumorigenesis is complicated not only by the existence of different protein forms but also by the changes of tumors over time and the treatment-induced alterations such as hormone ablation or chemotherapy[10,11,12]. CLU has been found to be dysregulated in many types of cancer including prostate and breast cancer[13,14,15]. Similarly, CLU was initially shown to be upregulated in Alzheimer's Disease (AD) and later observed to bind to amyloid beta peptides and preclude defibrilization of the amyloid peptides. Amongst its numerous functions in the brain, CLU aids in the clearance of amyloid-beta peptides and fibrils by binding to megalin receptors to enhance their endocytosis within glial cells[7]. Further, CLU is also present in lipoprotein particles and hence regulates cholesterol and lipid metabolism, which is compromised in the brains of AD patients[7].

Chronic allograft nephropathy (CAN) (chronic allograft injury/rejection) is of great concern in long term renal allograft survival. CAN differs from 'chronic rejection' in that it is an end point of tubular atrophy and interstitial fibrosis (IF/TA) in the graft caused by a series of immune and non-immune insults to the kidney, leading ultimately to graft failure.

Interstitial fibrosis is considered to be present when the supporting connective tissue in the renal parenchyma exceeds 5% of the cortical area.

Tubular atrophy refers to the presence of tubules with thick redundant basement membranes, or a reduction of greater than 50% in tubular diameter compared to surrounding non-atrophic tubules. IF/TA is contributed to by pre-existing donor factors such as donor age, underlying disease or donor-recipient size disparity; by immune factors involving acute and chronic humoral and cellular processes; or by post-transplant factors including drug toxicity and infection. A number of immune mechanisms contribute to CAN including acute and chronic alloantibody-mediated rejection as well as acute and chronic cellular rejection. The consequences of antibody mediated processes are a distinct set of histological features, mainly Transplant Glomerulopathy (TG), which is characterized by a doubling of the glomerular basement membrane (GBM), which is usually accompanied by IF/TA. Recurrent late acute cellular or antibody mediated rejection which is resistant to treatment is a critical predictor of CAN development.

What is needed in the art are markers whose expression can be used to identify patients suffering from kidney diseases and predict the development of kidney fibrosis. In addition, such markers are needed to identify renal allograft recipients who are at risk for developing IF/TA and represent targets for therapeutic intervention to prevent the development of IF/TA at an early stage, thereby preventing the development of CAN.

SUMMARY OF THE INVENTION

The present invention is based on the discovery that a specific urine biomarker, Clusterin, is predictive of poor graft function and chronic allograft dysfunction and for increased risk of developing IF/TA.

In one aspect, the present invention provides a method for identifying a kidney transplant recipient at an increased risk of developing fibrosis which comprise obtaining a post-transplant urine sample from the kidney transplant recipient; measuring the level of clusterin in the urine sample; comparing the level of clusterin in the patient sample to the level of clusterin in a control sample from the urine of a non-fibrotic kidney transplant recipient; and diagnosing a patient with a clusterin level that is significantly higher than the clusterin level in the control as being at an increased risk of developing interstitial fibrosis.

In another aspect, the present invention provides a method for identifying a kidney transplant recipient at an increased risk of developing tubular atrophy which comprises obtaining a post-transplant urine sample from the kidney transplant recipient; measuring the level of clusterin in the urine sample; comparing the level of clusterin in the patient sample to the level of clusterin in a control sample from the urine of a kidney transplant recipient that is not afflicted with tubular atrophy; and diagnosing a patient with a clusterin level that is significantly higher than the clusterin level in the control as being at an increased risk of developing tubular atrophy.

In a further aspect, the present invention provides a method for identifying a patient at increased risk of developing decreased renal function in a kidney transplant recipient which comprises the steps of obtaining a post-transplant urine sample from the patient; measuring the level of clusterin in the urine sample from the patient; comparing the level of clusterin in the sample to the level of clusterin in a control urine sample obtained from a non-fibrotic kidney transplant recipient; and diagnosing the patient as being at an increased risk of developing decreased renal function if the clusterin level in the patient's urine sample is more than 50% higher than the clusterin level in the control.

In yet a further aspect, the present invention provides a method for identifying a patient at increased risk of developing interstitial fibrosis or tubular atrophy which comprises the steps of obtaining a urine sample from the patient; measuring the level of clusterin in the urine sample; comparing the level of clusterin in the sample to the level of clusterin in a control urine sample from an individual not afflicted with interstitial fibrosis or tubular atrophy; and diagnosing the patient with a clusterin level that is significantly higher than the clusterin level in the control as being at an increased risk of developing tubular atrophy or interstitial fibrosis.

In yet a further aspect, the present invention provides a method for identifying a patient at increased risk of developing interstitial fibrosis or tubular atrophy which comprises the steps of obtaining a urine sample from the patient; measuring the level of clusterin in the urine sample; comparing the level of clusterin in the sample to the level of clusterin in a control urine sample from an individual not afflicted with interstitial fibrosis or tubular atrophy; and diagnosing the patient with a clusterin level that is at least 50% higher, and preferably 100% higher, than the clusterin level in the control as being at an increased risk of developing tubular atrophy or interstitial fibrosis.

In a still further aspect of the present invention the patient diagnosed as being at-risk for IF/TA is treated for interstitial fibrosis and/or tubular atrophy.

These and other aspects of the present invention will be apparent to those of ordinary skill in the art in light of the present description, claims and drawings.

DETAILED DESCRIPTION OF THE INVENTION

Definitions

Figure 1:
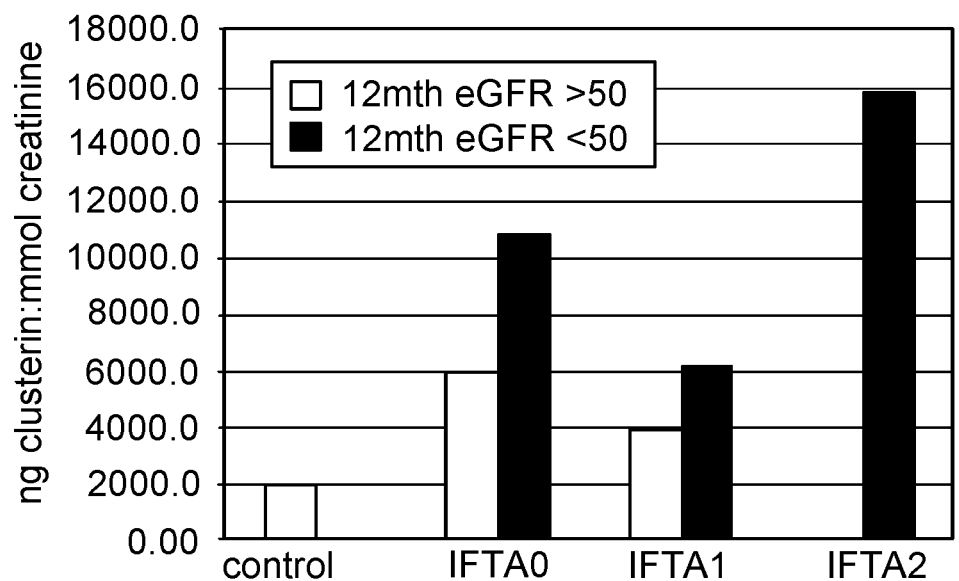
FIG. 1 is a graph comparing 3 month urine clusterin: creatinine concentrations vs 12 month IF/TA and 12 month eGFR. IF/TA 0, 1 and 2 correspond to no, mild, or moderate severity of fibrosis, respectively.

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude), preferably within a factor of two of a given value.

The term "significantly higher levels of Clusterin" is defined herein as at least 50%, and preferably 100% higher than in the control.

The present invention is based on the unexpected discovery that the levels of Clusterin in the urine of a kidney allograft recipient are significantly higher when compared to control urine samples obtained from kidney allograft recipient's urine who is not suffering from IF/TA. This is unexpected because before the present invention no such function had been ascribed to Clusterin.

The Clusterin protein (SEQ ID NOs: 1-5) found in the urine has now been identified as a member of a gene expression signature, which is predictive of IF/TA and decreased renal function in kidney recipients. Following urine collection and analysis at both 3 and 6 months post kidney transplant, a renal biopsy was performed at 1 year, the pathology read as per the Banff protocol[18,19] and compared to the analysis. The Banff classification characterizes five categories of renal allograft pathology: (1) antibody-mediated rejection; (2) suspicious of acute rejection; (3) acute rejection; (4) chronic sclerosing allograft nephropathy; and (5) other—changes not considered due to rejection.

It was observed that a higher urine Clusterin level at 3 and 6 months correlated with increased instances of IF/TA at the 12 month protocol biopsy. Similarly, lower urine Clusterin levels at 3 and 6 months were noted in patients with normal histology at 12 months.

Pursuant to the present invention Clusterin levels are measured in the urine of a kidney graft recipient. Preferably, soluble concentrations of clusterin in the patient's urine are assayed using a commercially available sandwich ELISA kit (Human Clusterin immunoassay, DCLUOO, R&D systems, UK) according to the manufacturer's instructions. In another embodiment, clusterin levels are measured in the urine of a patient believed to be at risk for IF/TA.

The clusterin level of the patient (transplant recipient or at-risk for IF/TA) is measured and compared to the clusterin level of a standard control (patient not afflicted with IF/TA). If the patient's measured clusterin level is significantly higher (at least 50% or more) than the control, the patient is diagnosed as being at-risk for IF/TA. The patient is then treated for interstitial fibrosis or tubular atrophy.

Further, renal function at 12 months also correlated with the 3- and 6-month Clusterin observation. Lower estimated glomarular filtration rate (eGFR), a measure of renal function, was noted in patients at 12 months who had significantly higher urinary Clusterin levels at 3 and 6 months. The results were consistent among various age, gender, transplant type and Delayed Graft Function (DGF) groups.

A patient identified as likely to develop fibrosis at the 12-month mark based on the 3-month Clusterin profile would provoke the necessary clinical steps required to inhibit or decrease progression of fibrosis development. In one embodiment, calcineurin inhibitors (CNIs), such as cyclosporine or tacrolimus, or a less fibrogenic immunosuppressive drug such as mycophenolate mofetil (MMF) or sirolimus, can be employed. In another embodiment, antifibrotic agents such as Pirfenidone (Esbriet), Relaxin, Bone morphogenetic protein 7 (BMP-7), Hepatocyte growth factor (HGF), or Epoetin delta can be administered to the patients identified as having elevated clusterin levels and increased risk of exposure to IF/TA[20,21].

Since patients who are identified as being at risk for developing IF/TA have impaired renal function and often suffer from hypertension, administration of an angiotensin converting enzyme inhibitor (ACEI) such as lisinopril or angiotensin II receptor antagonists such as losartan, to such patients is within the scope of the present invention.

In one embodiment of the invention, renal transplant patients are tested for the level of Clusterin in their urine at 3 months and 6 months post-transplant. The patient's Clusterin protein level is compared to a standard Clusterin level based on samples from renal transplant recipients that do not suffer from IF/TA. Patients identified as having Clusterin levels that are significantly higher (as defined above) than those in the Clusterin standard, are at increased risk of developing IF/TA and should receive appropriate treatment including, for example, anti-fibrotic agents.

The present invention is described below in working examples which are intended to further describe the invention without limiting the scope thereof.

In the Examples below the following materials and methods were used.

All kidney transplant recipients had anti-IL-2R mAb induction with Tacrolimus, mycophenolate, and prednisolone to maintain immune-suppression. This was the immunosuppression regimen for the patients that had Clusterin measured in the urine.

mRNA expression was determined by microarray on 160 biopsies of a 3-month protocol. The biopsies were performed for study purposes only to show a lack of renal dysfunction at the time. Utilizing the samples collected at 3 months, specific genes were determined to be associated with an increased CADI, an established measure of fibrosis which uses components of the BANFF score for renal transplant biopsies, and a decreased estimated Glomalular Filtration Rate (eGFR) at 1 year. Estimated GFR is based on creatinine and is a measure of renal function. Ninety-four biopsies with the 1-year endpoints were analyzed.

Example 1

Clusterin was observed to be highly associated with the development of fibrosis and the decline of renal function at the 12-month time point. Expression of Clusterin in the biopsy was not associated with fibrosis at the time of the 3-month biopsy but was associated with eGFR.

Clusterin was then measured in the urine. Soluble concentrations of Clusterin in the patient's urine were assayed using a commercially available sandwich ELISA kit (Human Clusterin immunoassay, DCLUOO, R&D systems, UK) according to the manufacturer's instructions. All urine samples were prepared at a 4-fold dilution and were run in duplicate. After the development of the colorimetric reaction, the OD at 450 nm was quantified by an eight-channel spectrophotometer, and the OD readings were converted to nanograms per milliliter (ng/ml) on the basis of the standard curves obtained with human Clusterin standard preparations. Clusterin concentrations were represented as "mean±SD".

The assay was done initially in 18 patients with 3-month urine and 12-month endpoint data (see FIG. 1). In addition, the data was analyzed from 29 renal transplant patients and utilized urine from different time points and at different levels of renal function to observe any correlation between the time post-transplant and renal function.

Concentrations of proteins in the urine can vary depending on how concentrated the urine sample is; hence, urinary Clusterin levels were normalized to creatinine in each sample. As shown in FIG. 1, increased concentration of Clusterin measured at 3 months correlated with higher instances of decreased renal function as noted by <50 (mL/min) of eGFR at the 12-month biopsy analysis. Further, higher instances of decreased renal function correlated with increased severity of IF/TA. In FIG. 1, IF/TA 0, 1 and 2 correspond to no, mild, or moderate severity of fibrosis, respectively.

Figure 2:
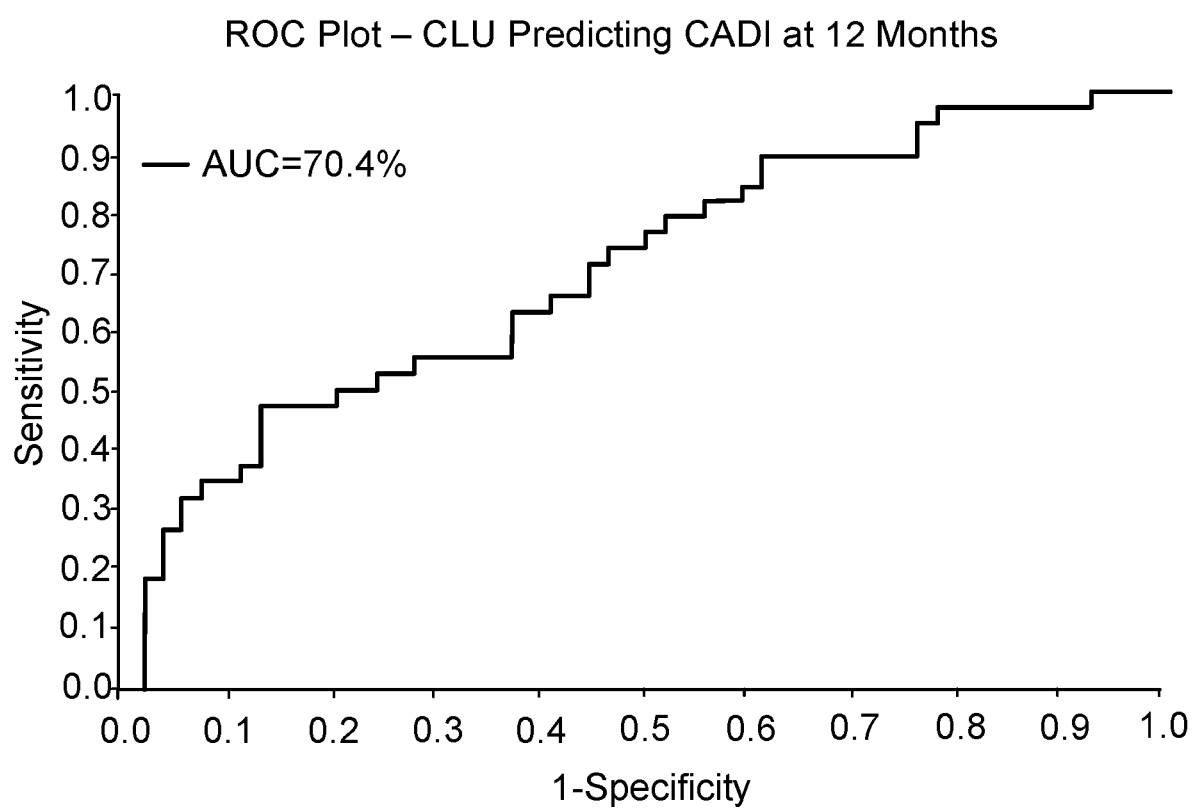
FIG. 2 is a graph displaying the ROC (Receiver Operating Characteristic) for the prediction of CADI (Chronic Allograft Damage Index) by intragraft mRNA expression. This is based on the microarray expression data.

FIG. 2 displays the ROC (Receiver Operating Characteristic) for the prediction of CADI (Chronic Allograft Damage Index) by intragraft mRNA expression. This is based on the microarray expression data. In FIG. 2, Sensitivity (y-axis) and Specificity (x-axis) are statistical measures of the performances of a binary classification test, also known in statistics as classification function. Sensitivity (also referred to as a "recall rate" in certain fields) measures the proportion of actual positives which are correctly identified as such (e.g. the percentage of sick people who are correctly identified as having the condition). Specificity measures the proportion of negatives which are correctly identified (e.g. the percentage of healthy people who are correctly identified as not having the condition). A perfect predictor would be described as having 100% specificity (i.e. not predicting anyone from the healthy group as sick); however all predictors have some error.

$$\text{Sensitivity} = \frac{\text{Number of true positives}}{\text{Number of true positives} + \text{number of false negatives}} =$$

probability of a positive test given that the patient is ill $$\text{Specificity} = \frac{\text{Number of true negatives}}{\text{Number of true negatives} + \text{number of false positives}} =$$

probability of a positive test given that the patient is well

Presented below in Tables 1 and 2 are the raw RNA data that is used to determine correlation with CADI.

TABLE 1

| Diagnostic Test | eGFR | CLU |
|---|---|---|
| AUC | 67.8% | 70.4% |
| Optimal Cut-Off Point | 9.0371 | 9.0457 |
| Sensitivity | 0.50 | 0.47 |
| Specificity | 0.22 | 0.87 |
| NPV | 0.39 | 0.70 |
| PPV | 0.31 | 0.72 |

Table 1 shows that intragraft expression of Clusterin is a more accurate predictor of fibrosis at the 12-month mark than the current standard of creatinine at 3 months. It compares urinary Clusterin at 3 months as a predictor of CADI as compared to eGFR at 3 months as a predictor of fibrosis at 3 months. As can be seen in Table 1, Clusterin had a higher Specificity (87%) than eGFR (22%).

Overall, Table 1 shows a correlation between Clusterin levels and eGFR.

eGFR is positive if eGFR<40 otherwise negative
CADI is positive if CADI>2 otherwise negative

TABLE 2

| Diagnostic Test | eGFR 12 Month Clu | CADI 12 Month Clu |
|---|---|---|
| AUC | 69.3% | 70.4% |
| Optimal Cut-Off Point | 9.0371 | 9.0457 |
| Sensitivity | 0.68 | 0.47 |
| Specificity | 0.70 | 0.87 |
| NPV | 0.93 | 0.70 |
| PPV | 0.28 | 0.72 |

Currently eGFR (e.g. creatinine) is used as a predictor of CADI at 12 months (see below). Clusterin is a more specific predictor of CADI at 12 months than eGFR as a predictor of CADI.

The AUC is 67.8%.
Optimal Cutpoint is 50.37
Sensitivity: 0.50
Specificity: 0.22
PPV: 0.31
NPV: 0.39

Presented below are the amino acid sequences of Clusterin isoforms 1-5 (SEQ ID NOS:1-5)

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description. Patents, patent applications, publications, product descriptions, and protocols are cited throughout this application, the disclosures of which are incorporated herein by reference in their entireties for all purposes.

REFERENCES

1. Wong P, Taillefer D, Lakins J, Pineault J, Chader G & Tenniswood M. 1994. Molecular characterization of human TRPM-2/clusterin, a gene associated with sperm maturation, apoptosis and neurodegeneration. European Journal of Biochemistry 221917-925
2. Jenne D E & Tschopp J. 1989. Molecular structure and functional characterization of a human complement cytolysis inhibitor found in blood and seminal plasma: identity to sulfated glycoprotein 2, a constituent of rat testis fluid. PNAS 867123-7127.
3. Cochrane D R, Wang Z, Muramaki M, Gleave M E & Nelson C C. 2007. Differential regulation of clusterin and its isoforms by androgens in prostate cells. Journal of Biological Chemistry 2822278-2287.
4. de Silva H V, Harmony J A, Stuart W D, Gil C M & Robbins J. 1990a. Apolipoprotein J: structure and tissue distribution. Biochemistry 295380-5389.
5. Reddy K B, Jin G, Karode M C, Harmony J A & Howe P H. 1996. Transforming growth factor beta (TGF beta)-induced nuclear localization of Apolipoprotein J/clusterin in epithelial cells. Biochemistry 356157-6163.
6. Shannan B, Seifert M, Leskov K, Willis J, Boothman D, Tilgen W & Reichrath J. 2006. Challenge and promise: roles for clusterin in pathogenesis, progression and therapy of cancer. Cell Death and Differentiation 1312-19.
7. Nuutinen T, Suuronen T, Kauppinen A, Salminen A. 2009. Clusterin: a forgotten player in Alzheimer's disease. Brain Res Rev: 89-104.
8. Devauchelle V, Essabbani A, De Pinieux G, Germain S, Tourneur L, Mistou S, Margottin-Goguet F, Anract P, Migaud H, Le Nen D, Lequerré T, Saraux A, Dougados M, Breban M, Fournier C, Chiocchia G. 2006. Characterization and functional consequences of underexpression of clusterin in rheumatoid arthritis. J Immunol. 6471-9.
9. Zhang, H, Kim, J, Edwards, C, Xu, Z, Taichman, R and Wang, C. 2005. Clusterin inhibits apoptosis by interacting with activated Bax. Nature Cell Biology 909-915.
10. Miyake H, Nelson C, Rennie P, and Gleave M E. 2000b. Testosterone-repressed prostate message-2 is an antiapoptotic gene involved in progression to androgen independence in prostate cancer. Cancer Research 60170-176.
11. Mallory J C, Crudden G, Oliva A, Saunders C, Stromberg A and Craven R J. 2005. A novel group of genes regulates susceptibility to antineoplastic drugs in highly tumorigenic breast cancer cells. Molecular Pharmacology 681747-1756.
12. Cappelletti V, Gariboldi M, De Cecco L, Toffanin S, Reid J F, Lusa L, Bajetta E, Celio L, Greco M, Fabbri A et al. 2008. Patterns and changes in gene expression following neo-adjuvant anti-estrogen treatment in estrogen receptor-positive breast cancer. Endocrine-Related Cancer 15439-449.
13. Redondo M, Villar E, Torres-Munoz J, Tellez T, Morell M & Petito C K. 2000. Overexpression of clusterin in human breast carcinoma. American Journal of Pathology 157393-399.
14. Bettuzzi S, Davalli P, Astancolle S, Carani C, Madeo B, Tampieri A and Corti A. 2000. Tumor progression is accompanied by significant changes in the levels of expression of polyamine metabolism regulatory genes and clusterin (sulfated glycoprotein 2) in human prostate cancer specimens. Cancer Research 6028-34.
15. Rizzi, F and Bettuzzi, S. 2010. The Clusterin Paradigm in Prostate and Breast Carcinogenesis. Endocrine-Related Cancer R1-R17.
16. Kallon, Delordson. Histocompatibility & Immunogenetics—a collection of brief revision notes. http://www.histocompatibilityandimmunogenetics.com/17.
17. K. Solez, R. B. Colvin, L. C. Racusen, B. Sis, P. F. Halloran, P. E. Birk, P. M. Campbell, M. Cascalho, A. B. Collins, A. J. et al. 2007. Chronic Allograft Injury and Elimination of Chronic Allograft Nephropathy: Chronic Alloimmune Injury/Rejection versus Non-Immune Injury. American Journal of Transplantation. 2007 518-526.
18. Isoniemi H, Taskinen E, Hayry P. 1994 Histological chronic allograft damage index accurately predicts chronic renal allograft rejection. Transplantation 1195-8.
19. Solez et al. 2008. Banff 07 Classification of Renal Allograft Pathology: Updates and Future Directions. American Journal of Transplantation 753-760.
20. Negri, A L. 2004. Prevention of progressive fibrosis in chronic renal diseases: antifibrotic agents. J Nephrol. 496-503.
21. De Beuf A, D'Haese P C, Verhulst A. 2010. Epoetin delta as an antifibrotic agent in the remnant kidney rat: a possible role for transforming growth factor beta and hepatocyte growth factor. Nephron Exp Nephrol. e46-59.

What is claimed is:

1. A method for identifying a kidney transplant recipient at an increased risk of developing interstitial fibrosis or tubular atrophy which comprises:
    detecting the level of clusterin in a post-transplant urine sample from the kidney transplant recipient;
    detecting the level of clusterin in a control sample from the urine of a non-fibrotic kidney transplant recipient; and
    identifying said kidney transplant recipient with a clusterin level that is significantly higher than the clusterin level in the control as being at an increased risk of developing interstitial fibrosis or tubular atrophy.

2. The method of claim 1 which comprises treating the recipient identified as being at an increased risk of developing interstitial fibrosis or tubular atrophy for interstitial fibrosis or tubular atrophy.

3. The method of claim 2 wherein the treatment comprises administering an anti-fibrotic agent to the recipient identified as being at increased risk of developing interstitial fibrosis or tubular atrophy.

4. The method of claim 3 wherein the anti-fibrotic agent is a member selected from the group consisting of Pirfenidone, Relaxin, Bone morphogenetic protein 7 (BMP-7), Hepatocyte growth factor (HGF), and Epoetin delta.

5. The method of claim 1 comprising administering an angiotensin converting enzyme inhibitor (ACEI) to the recipient identified as being at increased risk of developing interstitial fibrosis or tubular atrophy.

6. The method of claim 5 comprising administering an angiotensin II receptor antagonist to the recipient identified as being at increased risk of developing interstitial fibrosis or tubular atrophy.

7. The method of claim 6 wherein said angiotensin II receptor antagonist is losartan.

8. The method of claim 2 comprising administering an immunosuppressive drug to the recipient identified as being at increased risk of developing interstitial fibrosis or tubular atrophy.

9. The method of claim 8 wherein said immunosuppressive drug is a member selected from the group consisting of cyclosporine, tacrolimus, mycophenolate mofetil (MMF) and sirolimus.

10. A method for identifying a kidney transplant recipient at an increased risk of developing tubular atrophy which comprises:
   detecting the level of clusterin in a post-transplant urine sample from the kidney transplant recipient;
   detecting the level of clusterin in a control sample from the urine of a kidney transplant recipient that is not afflicted with tubular atrophy; and
   identifying said patient with a clusterin level that is significantly higher than the clusterin level in the control as being at an increased risk of developing tubular atrophy.

11. The method of claim 10 which comprises treating the kidney transplant recipient identified as being at an increased risk for developing tubular atrophy for the tubular atrophy.

12. A method for identifying a kidney transplant recipient that is afflicted with tubular atrophy and at an increased risk of developing decreased renal function which comprises the steps of:
   detecting the level of clusterin in a post-transplant urine sample from the kidney transplant recipient that is afflicted with tubular atrophy;
   detecting the level of clusterin in a control urine sample from a non-fibrotic kidney transplant recipient; and
   identifying the kidney transplant recipient that is afflicted with tubular atrophy as being at an increased risk of developing decreased renal function when the clusterin level in said transplant recipient's urine sample is more than 50% higher than the clusterin level in the control.

13. The method of claim 12 further comprising treating the kidney transplant recipient identified as being at an increased risk of developing decreased renal function for decreased renal function.

14. The method of claim 13 wherein the treatment comprises administering an anti-fibrotic agent to the recipient identified as being at an increased risk of developing decreased renal function.

15. The method of claim 14 wherein the anti-fibrotic agent is a member selected from the group consisting of Pirfenidone, Relaxin, Bone morphogenetic protein 7 (BMP-7), Hepatocyte growth factor (HGF), and Epoetin delta.

16. A method for identifying a kidney transplant recipient at an increased risk of developing interstitial fibrosis or tubular atrophy which comprises the steps of:
   detecting the level of clusterin in a post-transplant urine sample obtained from the kidney transplant recipient; and
   identifying said kidney transplant recipient with a clusterin level that is significantly higher than the clusterin level in a control urine sample as being at an increased risk of developing tubular atrophy or interstitial fibrosis-; and
   treating the kidney transplant recipient by administering sirolimus to said recipient;
   wherein said control urine sample is from an individual not afflicted with interstitial fibrosis or tubular atrophy.

* * * * *